(12) United States Patent
Ling et al.

(10) Patent No.: US 8,735,363 B2
(45) Date of Patent: May 27, 2014

(54) PREPARATION AND APPLICATION OF HEPARIN SILVER

(75) Inventors: Peixue Ling, Shandong (CN); Yanli He, Shandong (CN); Jianying Chen, Shandong (CN)

(73) Assignee: Peixue Ling, Shandong (CN)

( * ) Notice: Subject to any disclaimer, the term of this patent is extended or adjusted under 35 U.S.C. 154(b) by 1274 days.

(21) Appl. No.: 11/912,123

(22) PCT Filed: Apr. 20, 2006

(86) PCT No.: PCT/CN2006/000742
§ 371 (c)(1),
(2), (4) Date: May 6, 2008

(87) PCT Pub. No.: WO2006/111092
PCT Pub. Date: Oct. 26, 2006

(65) Prior Publication Data
US 2008/0269164 A1    Oct. 30, 2008

(30) Foreign Application Priority Data

Apr. 20, 2005   (CN) .......................... 2005 1 0043256

(51) Int. Cl.
| | | |
|---|---|---|
| *A01N 43/04* | (2006.01) | |
| *A61K 31/70* | (2006.01) | |
| *A61K 9/50* | (2006.01) | |
| *C08B 37/10* | (2006.01) | |

(52) U.S. Cl.
USPC ............................... 514/36; 424/499; 536/21

(58) Field of Classification Search
USPC ................ 514/56; 424/499; 536/21
See application file for complete search history.

(56) References Cited

U.S. PATENT DOCUMENTS

| 3,932,627 A | 1/1976 | Margraf |
|---|---|---|
| 2002/0146446 A1 | 10/2002 | Solomon |

FOREIGN PATENT DOCUMENTS

| CN | 1 554 671 | 12/2004 |
|---|---|---|
| CN | 1 580 080 | 2/2005 |
| CN | 1687141 A | 10/2005 |
| DE | 4302053 C1 | 6/1994 |
| GB | 2 365 443 | 12/2004 |
| IT | 1 269 665 | 4/1997 |
| JP | 10-152579 | 6/1998 |
| JP | 2003-048840 | 2/2003 |
| WO | WO9851273 A1 | 11/1998 |
| WO | WO02083086 A1 | 10/2002 |

OTHER PUBLICATIONS

Huang, H., Yang, X. (2004) Synthesis of polysaccharide-stabilized gold and silver nanoparticles: a green method. Carbohydrate Research, vol. 339, p. 2627-2631.*
Baker, C., Pradhan, A., Pakstis, L., Pochan, D.J., Ismat Shah, S. (2005) Synthesis and Antibacterial Properties of Silver Nanoparticles. Journal of Nanoscience and Nanotechnology, vol. 5, p. 244-249.*
Reyes, A.E. Astiazaran, J.A., Chavez, C.C., Jaramillo, F., Saliba, M.J. (2001) Burns Treated with and Without Heparin: Controlled Use in a Thermal Disaster. Annals of Burns and Fire Disasters, vol. XIV, No. 4.*
Klasen, H.J. (2000) A historical review of the use of silver in the treatment of burns. II. Renewed interest for silver. Burns, vol. 26, p. 131-138.*
Limayem, I., Charcosset, C., Fessi, H. (2004) Purification of nanoparticle suspensions by a concentration/diafiltration process. Separation and Purification Technology, vol. 38, p. 1-9.*
Remington's The Science and Practice of Pharmacy, 19th Edition, editor Alfonso R. Gennaro, published by Mack Publishing Company (1995) p. 1544-1545.*
Chen, J., Han, C.M., Lin, X.W., Tang, Z.J., Su, S.J. (2006) Effect of silver nanoparticle dressing on second degree burn wound. Chinese Journal of Surgery (Zhonghua Wai Ke Za Zhi), vol. 44, No. 1, p. 50-52.*
Brown et al., "Enhancement of wound healing by topical treatment with epidermal growth factor," *N. Engl. J Med.*, 321:76-79, 1989.
European Search Report; Nov. 23, 2012; European Patent Office (EPO); 06741691.7; 13 pages.

* cited by examiner

*Primary Examiner* — Scarlett Goon
(74) *Attorney, Agent, or Firm* — Fish & Richardson P.C.

(57) ABSTRACT

The present invention relates to a method for preparation of heparin silver, to use of heparin silver in manufacture of medicine for treating burns and/or scalds, to a method of using heparin silver to treat burns and/or scalds, and to a topical preparation containing heparin silver for treating burns and/or scalds. The heparin silver product prepared according to the method of the present invention has a high purity and less impurity. The animal test proved that the medicine made by using heparin silver exhibited effects of accelerating wound healing and reducing scar formation.

7 Claims, No Drawings

US 8,735,363 B2

PREPARATION AND APPLICATION OF HEPARIN SILVER

CROSS-REFERENCE TO RELATED APPLICATIONS

This application is a National Stage application under 35 U.S.C. §371 and claims benefit under 35 U.S.C. §119(a) of International Application No. PCT/CN2006/000742 having an International Filing Date of Apr. 20, 2006, which claims benefit of CN 20050043256.1 filed on Apr. 20, 2005, both of which are incorporated by reference in their entirety herewith.

TECHNICAL FIELD

The present invention pertains to medical technical field, in particular relates to a method for preparing heparin silver, a use of heparin silver in the manufacture of a medicament for treating burns and/or scalds, a method of using heparin silver in the treatment of burns and/or scalds, and a preparation containing heparin silver for treating burns and/or scalds.

BACKGROUND ART

Heparin is derived from animal tissues, is a sulfated glycosaminoglycan, and has a complex structure. The basic framework of sulfated glycosaminoglycan is a polysaccharide chain consisting of repeated disaccharide units linked with uronic acids and glucosamine through glycosidic bonds, wherein glycuronic acids include iduronic acid and glucuronic acid, monosaccharide residues each is sulfated and acetated in various situations, such as N-sulfate group, N-acetate group, and O-sulfate groups (ester) at different positions. Heparin that is not fractioned has a molecular weight ranging from 3,000 to 30,000 Dalton, and an average molecular of 12,000-15,000 Dalton. Heparin with a molecular weight of 3,000-8,000 Dalton is called as low molecular weight heparin. The most important physiologic activities of heparin are anticoagulant activity and antithrombotic activity, and the side-effects of heparin include platelet reduction and hemorrhage. Low molecular weight heparin has a decreased antithrombase activity and thus can reduce the risk of bleeding when the thrombosis is prevented. In addition, it also has a high bioavailability and long half-life in vivo, so that it draws a lot of attention in the development of heparin products.

Heparin products on market currently include heparin sodium and heparin calcium in forms such as injectable solution, cream, buccal tablets, etc., while other heparin salts are not used in clinic at present. Heparin has been used in clinic for about 70 years mainly for anticoagulation, prevention of thrombosis diseases and improvement of topical microcirculation. The most important side-effect of heparin is hemorrhage, so that the contraindications of heparin include active bleeding and ulcer, heparin allergy, platelet reduction, bleeding status, etc. It has been confirmed with experiments that the safety ranged for clotting time tested each day before application of heparin is 15-30 minutes when heparin was used in large amount during early stages (ischemia and acidosis stages) after burn, and no positive result of anticoagulation was observed when heparin was topically used from early stage after burn until wound surface healed.

At present, heparin sodium is used on skin in clinic for the treatment of superficial phlebitis, varicose phlebitis, adjunctive therapy for varicosis and phlebosclerosis, hematoma, contused wound, swelling and edema, thrombophletitis, exudation caused by intravenous transfusion or injection, soft tissue contusion, chilblain, alligatoring, eczema, inhibition of scarring and softening scar. However, no reference has been found that publicly disclosed a method for preparing heparin silver, a use of heparin silver in the manufacture of a medicament for treating burns and/or scalds, a method of using heparin silver in the treatment of burns and/or scalds, and a preparation containing heparin silver for treating burns and/or scalds.

CONTENTS OF THE INVENTION

The object of the present invention is to provide a method for preparing heparin silver, and a use of heparin silver, especially the heparin silver prepared according to the method of the present invention in the manufacture of a medicament for treating burns and/or scalds. The animal test proved that the said heparin silver is applicable in the treatment of burns and/or scalds, and exhibits advantages such as accelerating healing speed, reducing occurrence of infection and inflammation, and improving healing quality of wound surface, etc.

The method for preparing heparin silver according to the present invention comprises:

(1) dissolving a soluble heparin salt in deionized water to obtain a heparin salt solution;
(2) adding silver nitrate into the solution obtained in step (1), stirring and dissolving;
(3) concentrating the solution obtained in step (2) under vacuum to precipitate heparin silver, then filtrating to collect deposit;
(4) dissolving the deposit obtained in step (3) in deionized water, then purifying it by dialysis or ultrafiltration;
(5) concentrating the solution obtained in step (4) under vacuum to obtain a concentrated solution of heparin silver; and
(6) freeze-drying the concentrated solution obtained in step (5), or dewatering by adding an organic solvent, collecting deposit and conventionally drying under vacuum to obtain a finished product.

In the said method for preparing heparin silver, the soluble heparin salt is selected from a group consisting of heparin sodium, heparin potassium, heparin calcium, heparin zinc or a mixture thereof.

In the said method for preparing heparin silver, the amount of the added silver nitrate is 50-800%, preferably 150-600%, more preferably 200-500% by weight based on the soluble heparin salt in the solution.

In the said method for preparing heparin silver, the organic solvent in step (6) is selected from pharmaceutically acceptable conventional organic solvents or a mixture thereof, preferably ethanol, acetone, methanol or a mixture thereof, more preferably ethanol.

In the preparation and extraction of heparin salt, an organic solvent such as ethanol, methanol and/or acetone or a mixture thereof is usually used in precipitation, dewatering and drying. In the method for preparing heparin silver according to the present invention, silver nitrate with a relatively high solubility is used as raw material, which can provide sufficient free silver ions in reaction solution and thus facilitates the formation and precipitation of heparin silver. In the meantime, due to the existence of silver ions in reaction solution, the added organic solvent such as ethanol, methanol or acetone may for explosive fulminic acid. Thus, it is better not to use these organic solvents directly for precipitation and dewatering. In the present invention, a method of concentration is employed in precipitation of heparin silver with a relatively low solubility, and in filtration, wherein the filtrate can be recovered and reused repeatedly. The obtained deposit is dissolved in deionized water again, dialysis or ultrafiltration is employed to remove impurities (including residual sodium ions, absorbed silver ions and nitrate ions) in the deposit, then the solution is concentrated under vacuum again and dewatered by using an organic solvent or freeze-dried.

The heparin silver prepared according to the method of the present invention has a high purity and less impurities, wherein silver ion content is 25-45%, sodium ion content is less than 2.5%, and nitrate content is less than 0.1%.

After pulverization and sterilization, the heparin silver as prepared according to the method of the present invention can be directly applied to wound surface of burns and/or scalds, or be formulated together with other drugs and conventional excipients to form a pharmaceutical preparation for the treatment of burns and/or scalds, which can be applied to wound surface of burns and/or scalds in order to achieve purposes such as accelerating healing speed, reducing occurrence of infection and inflammation, improving healing quality of wound surface, etc. The pharmaceutical preparation of the present invention can be a powder, ointment, patch, etc., preferably a powder, which may comprise pharmaceutically acceptable excipients commonly used in a topical pharmaceutical preparation. The present invention further relates to a method for the treatment of burns and/or scalds, wherein a topical formulation containing heparin silver is coated on the afflicted parts.

When heparin is used for the treatment of burns, it can alleviate pain, prevent coagulation, inhibit inflammation, promote neovascularization, recover local blood-supply, influence the synthesis and degradation of collagen, lead to smooth skin after healing of wound surface, reduce scars and cicatricial contracture, prevent barrier function of intestinal tract, prevent and improve lung and kidney functions, enhance immunity of human body, prevent infection, etc. Silver salt exhibits astriction after it is applied to wound surface of skin, can make wound surface dry, and promote incrustation and healing. When heparin silver is applied to wound surface of burn and/or scald, it exhibits functions of both heparin and silver salt and significantly accelerate healing speed, reduce infection and inflammation, and improve healing quality of wound surface.

Specific Modes for Carrying Out the Invention

EXAMPLE 1

0.3 kg heparin sodium (comprising 60-70% by weight of heparin having an average molecular weight less than 8,000 Da; having an anti-FXa activity of 2.3 times the anti-FIIa activity, wherein by employing the method stipulated in the tentative standard, WS-487(X-423)-2001 of the State Food and Drug Administration, the FIIa potency was tested according to the sheep blood plasma and the FXa potency was tested in according to COATEST kit method) was dissolved in 10 liters deionized water. Under lucifugal condition, the following steps were conducted: adding 1.2 kg silver nitrate, reacting at room temperature under stirring for 2 hours, vacuum concentrating at 35-40° C. until the reaction solution was reduced to a volume of about 3 liters, filtrating the reaction solution with a 0.8 μm microporous filtration membrane, storing the filtrate for recovery, dissolving the deposit in 0.3 liters deionized water under stirring, dialyzing with deionized water for 24 hours by using a dialysis membrane having a cut-off molecular weight of 3,000, vacuum concentrating again until the solution volume was reduced to about 0.2 liters, and freeze-drying to obtain product. The product was pulverized, passed through a 200 mesh screen, packaged with air-permeation paper, sterilized with ethylene oxide, and further packaged with double-layer plastic film bag to obtain the finished product.

EXAMPLE 2

0.3 kg heparin sodium (having an average molecular weight of 12,000-15,000 Da; having a potency of 156 IU/mg, which was tested according to the biological assay of heparin as stipulated in Appendix XIID of the Pharmacopoeia of People's Republic of China Edition 2000) was dissolved in 10 liters deionized water. Under lucifugal condition, the following steps were conducted: adding 1.1 kg silver nitrate, reacting at room temperature under stirring for 2 hours, vacuum concentrating at 35-40° C. until the reaction solution was reduced to a volume of about 3 liters, filtrating the reaction solution with a 0.8 μm microporous filtration membrane, storing the filtrate for recovery, dissolving the deposit in 0.5 liters deionized water under stirring, ultrafiltrating by using an ultrafiltration membrane having a cut-off molecular weight of 2,000, adding supplementary deionized water 0.1 liters when the solution volume was reduced to 0.4 liters during the ultrafiltration, ultrafiltrating to obtain about 0.3 liters solution after adding supplementary deionized water for three times, vacuum concentrating again until the solution volume was reduced to about 0.2 liters, dewatering by adding 3.5 times of ethanol, precipitating, vacuum drying the deposit at 35-40° C. to obtain product. The product was packaged with double-layer plastic film bag to obtain the finished product.

According to the methods used in Examples 1 and 2, similar results were obtained when heparin potassium, heparin calcium, heparin zinc of mixtures thereof were used.

EXAMPLE 3

Measurement of Silver Nitrate Product

1. Method for Measurement of Silver Ion
    Titration was employed in the method, which comprised weighing about 0.5 g heparin silver, dissolving by adding 8 ml nitric acid, adding 50 ml water and 2 ml ammonium ferric sulfate indication solution, titrating with 0.1 mol/L ammonium thiocyanate volumetric solution, wherein per 1 ml of 0.1 mol/L ammonium thiocyanate volumetric solution was equivalent to 10.79 mg silver. The silver ion content was calculated by dividing the amount of silver with the amount of heparin silver where the water content was reduced. The water content was determined by the loss on drying, wherein the sample was dried at 105° C. to constant weight (according to the Pharmacopoeia of People's Republic of China Edition 2005). The indication solution and volumetric solution were prepared according to the Pharmacopoeia of People's Republic of China Edition 2005.
2. Method for Measurement of Sodium Ion
    It was measured by atomic absorption spectrophotometry or plasma emission spectroscopy (see the Appendix of the Pharmacopoeia of People's Republic of China Edition 2005).
3. Measurement Determination of Residual Nitrate Content
    (1) Measurement by coloration method: preparing 0.2%, 0.15%, 0.1%, 0.08% and 0.05% nitrate solutions, separately taking 2 ml, adding equivalent amount of sulfuric acid and mixing, adding ferrous sulfate solution along wall, observing the coloration at the interface between two solutions, wherein brown color did not appear when nitrate concentration was less than 0.1%, that was the detection limit of the coloration method was 0.1%. Heparin silver 2 g was dissolved in 50 ml deionized water, degraded by γ-ray, concentrated and crystallized to remove saccharide, and the solution was further concentrated to 2 ml and tested according to the said coloration method.

(2) Measurement by ion chromatography (see the Appendix of the Pharmacopoeia of People's Republic of China Edition 2005): the detection limit was 50 ppm.

The determined data of the products of Examples 1 and 2 are shown in Table 1.

TABLE 1

| Sample | Example 1 | Example 2 |
|---|---|---|
| Silver ion content | 35.2% | 30.8% |
| Sodium ion content | 0.48% | 1.22% |
| Nitrate content | Less than 0.1% | Less than 0.1% |
| Water content | 6.70% | 8.45% |

EXAMPLE 4

Animal Test for the Treatment of Burns and/Scalds by Using Heparin Silver

1. Animal Model of Hyperplastic Scar

Long-term scar model was established by excising 2 cm×5 cm whole-thickness skin from New-Zealand rabbit's ventral surface to form wound surface (see specific steps in the reference: Morris, (1997), Acute and chronic animal models for excessive dermal scarring: quantitative studies). The control group was treated by dressing wound surface with sulfadiazine silver powder, and the dressing was changed once per week. The healing situation was observed after 12 months from excision, and the healing standard was that the scab was less than 5% of area of wound surface. The scar tissue was subjected to Masson staining and observed under light microscope, and the thickness of dermis (Da) of wound surface after epithelization and the thickness of dermis (Db) of adjacent normal tissue were measured. The scar index was calculated as=(Da−Db)/Db.

The results are shown in Table 2.

TABLE 2

| Group | Control Group | Test Group |
|---|---|---|
| Healing time of wound surface (days) | 26.5 ± 2.59 (n = 6) | 21.4 ± 2.16 (n = 6)* |
| Scar index, 60 days | 2.83 ± 0.46 (n = 6) | 2.06 ± 0.83 (n = 6) |
| 180 days | 3.46 ± 0.76 (n = 6) | 1.85 ± 0.52 (n = 6)* |

*As compared to the control group, difference is significant ($p < 0.05$).

2. Animal Model of Burn

Rats were intraperitoneally anesthetized with 5% chloral hydrate, depilated on back, scalded with 90° C. steam for 10 seconds to cause 20% area of deep second degree scald (see specific steps in the reference "New Technology and Healing Mechanism for Wound Surface of Burns", Edited by Lu Shuliang, 2003), and the rats were intraperitoneally injected with 1 ml physiologic saline to supply blood volume after rats were wounded for 1 hour. Rats of the control group were treated by dressing wound surface with sulfadiazine silver powder until the rats in the group are healed, wherein the dressing had a thickness of 0.5-1 mm and was changed once per day. The rats of test groups were treated by addressing wound surface with heparin silver powder (the product of Example 1) until they are healed, wherein the dressing had a thickness of 0.5-1 mm and was changed once per day. After rats were wounded, samples were taken at intervals of time. The wet weight of wound surface tissue (Ga) and the tissue dry weight (Gb) after baking at 80° C. for 72 hours were measured by weighting method. The water content of wound surface was calculated as W=(Ga−Gb)/Ga×100%, wherein W represented the degree of edema. The hydroxyproline content of wound surface was measured according to chloramine T oxidization method (see Xu Zhiqin (1990), "Improvement of measurement of hydroxyproline in tissue"). The hydroxyproline content reflected the collagen content of wound surface.

The results are shown in Table 3.

TABLE 3

| Group | | Normal Group | Test Group | Control Group |
|---|---|---|---|---|
| Healing Time (d) | | — | 21.5 ± 2.2 (n = 8) # | 25.0 ± 1.7 (n = 8) |
| Hydroxyproline content of wound surface (ug/mL) | | 18.37 ± 1.27 (n = 5) | — | — |
| | 1 d | — | 18.55 ± 2.13 (n = 5) | 17.65 ± 2.66 (n = 5) |
| | 2 d | — | 20.45 ± 2.12 (n = 5) | 18.37 ± 2.41 (n = 5) |
| | 3 d | — | 22.04 ± 1.35 (n = 5) | 18.86 ± 1.92 (n = 5) |
| | 5 d | — | 23.27 ± 2.11 (n = 6) | 21.71 ± 2.05 (n = 5) |
| | 7 d | — | 23.96 ± 2.54 (n = 6) | 22.57 ± 2.82 (n = 5) |
| | 10 d | — | 26.87 ± 2.36 (n = 6) *# | 22.12 ± 2.65 (n = 6) |
| | 14 d | — | 26.91 ± 2.14 (n = 6) * | 23.94 ± 1.88 (n = 6) |
| | 21 d | — | 24.05 ± 1.74 (n = 7) * | 25.63 ± 2.95 (n = 6) |
| Water content of wound surface (W) | | 67.28 ± 1.86 (n = 5) | — | — |
| | 8 h | — | 80.25 ± 2.78 (n = 6) * | 80.37 ± 1.56 (n = 6) * |
| | 24 h | — | 70.82 ± 3.56 (n = 6) *# | 76.15 ± 3.21 (n = 6) * |
| | 48 h | — | 70.16 ± 2.64 (n = 6) | 72.23 ± 2.37 (n = 6) * |
| | 72 h | — | 68.44 ± 1.32 (n = 5) | 68.75 ± 2.89 (n = 5) |
| | 5 d | — | 67.61 ± 2.85 (n = 5) | 68.69 ± 2.18 (n = 5) |
| | 7 d | — | 67.52 ± 1.36 (n = 5) | 68.05 ± 2.23 (n = 5) |

As compared to the control group, the difference was significant ($p < 0.05$)
* As compared to the control group, the difference was significant ($p < 0.01$)

What is claimed is:

1. A method for the treatment of a burn and/or a scald, comprising applying a topical preparation containing heparin silver to the burn and/or scald, wherein the heparin silver is prepared according to a method comprising:

(a) dissolving a soluble heparin salt in deionized water to obtain a heparin salt solution;

(b) adding silver nitrate into the solution obtained in step (a), stirring at room temperature and dissolving;

(c) concentrating the solution obtained in step (b) under vacuum at 35-40° C. to precipitate heparin silver, then filtrating to collect the deposit;

(d) dissolving the deposit obtained in step (c) in deionized water, then purifying it by dialysis or ultrafiltration;

(e) concentrating the solution obtained in step (d) under vacuum at 35-40° C. to obtain a concentrated solution of heparin silver; and (f) freeze-drying the concentrated solution obtained in step (e), or dewatering by adding an organic solvent, collecting the deposit and conventionally drying under vacuum to obtain a finished product;

wherein the amount of the added silver nitrate in step (b) is 150-600% by weight of the soluble heparin salt in the solution.

2. The method according to claim 1, wherein the preparation is in the form of a powder, ointment or patch.

3. The method according to claim 1, wherein the soluble heparin salt in step (a) is selected from the group consisting of heparin sodium, heparin potassium, heparin calcium, heparin zinc or a mixture thereof.

4. The method according to claim 1, wherein the soluble heparin salt in step (a) is heparin sodium.

5. The method according to claim 1, wherein the amount of the added silver nitrate in step (b) is 200-500% by weight of the soluble heparin salt in the solution.

6. The method according to claim 1, wherein the organic solvent in step (f) is ethanol, acetone, methanol or a mixture thereof.

7. The method according to claim 1, wherein the organic solvent in step (f) is ethanol.

* * * * *